US00PP09886P

United States Patent [19]

Leighfield

[11] Patent Number: Plant 9,886

[45] Date of Patent: May 6, 1997

[54] POINSETTIA PLANT NAMED 'WHITE SAILS'

[75] Inventor: William Leighfield, Brownsville, Canada

[73] Assignee: Fernlea Flowers, Ltd., Canada

[21] Appl. No.: 534,193

[22] Filed: Sep. 26, 1995

[51] Int. Cl.[6] ..... A01H 5/00

[52] U.S. Cl. ..... Plt./86.2

[58] Field of Search ..... Plt./86.2

[56] References Cited

U.S. PATENT DOCUMENTS

P.P. 7,801 2/1992 White ..... Plt./86.2

*Primary Examiner*—James R. Feyrer

*Attorney, Agent, or Firm*—Webb Ziesenheim Bruening Logsdon Orkin & Hanson, P.C.

[57] ABSTRACT

A poinsettia plant named "White Sails" particulaly characterized by is brilliant cream colored bracts agains a background of dark green foliage, its strong, fixed stems, its long lasting keeping qualities in the home, its excellent resisance to fade, vigorous growth habits and its branch and bract production.

1 Drawing Sheet

BACKGROUND OF THE NEW PLANT

The present invention comprises a new and distinct cultivar of *Euphorbia pulcherrima* known by the varietal name "White Sails".

The new cultivar was discovered in a large population of the cultivar Red Sails (U.S. Pat. No. P.P. 6,980) in 1987 at Delhi, Ontario. The new cultivar is believed to be a sport of the culivar Red Sails. The new cultivar was first asexually reproduced by cuttings by Fernlea Flowers, Ltd. of Delhi, Ontario in early 1988 and has been field tested and repeatedly asexually reproduced by cuttings by Fernlea Flowers, Ltd. of Delhi, Ontario. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Eight week response time
2. Dark green foliage.
3. Cream colored bracts.
4. Thick strong stems.
5. Large bracts.
6. Same dark green foliage and flowering response as Red Sails.
7. Cyathia is larger than Red Sails.
8. Stems are thicker than Red Sails.
9. Bracts up to 4.5 inches wide and 8 inches long
10. Outstanding disease resistance.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Delhi, Ontario. The plant history was taken on eight week plants. The test plants were grown under normal greenhouse conditions and color readings were taken under natural greenhouse light. Color references are from the Exotica International Pictorial Encyclopedia of Exotic Plants Series No. 4.

The plant:

*Form.*—Compact, free branching when pinched.

*Growth habit.*—Thick strong stems; compact with very little growth regulation.

*Rooting habit.*—Fast, vigorous root system.

*Blooming habit.*—Same as Red Sails.

*Blooming season.*—Same as Red Sails; best grown at 64° to 68° F.

Foliage:

*Size.*—Width: 3 to 4 inches. Length: 5 to 7 inches.

*Color.*—New foliage — Upper side, 83 Fern Green. Under side, 76 Meadow Green. Mature foliage — Upper side, shade darker than 70 Ivy Green. Under side, 77 Forest Green.

*Shape.*—Pointed lobes, broad.

*Texture.*—Fleshy. Upper side, smooth velvety. Under side, smooth evenly veined.

*Edge of margin.*—Slightly serrated.

*Ribs and veins.*—Color, 72 Spring green.

*Disease resistance.*—Outstanding.

Flower:

*Quantity.*—15 to 18 cyathia per stem.

*Color.*—3 Canary.

*Size.*—Above average compared to Red Sails.

*Shape.*—Peduncle is elongated therefore cyathia are more upright and visible.

Bracts:

*Size.*—Large. Width (in bloom): 4.5 inches. Length (in bloom): 8 inches.

*Shape.*—Pointed lobes, broad.

*Texture.*—Upper side, velvety. Under side, smooth.

*Color.*—Upper side, 1 Cream. Under side, 1 Cream.

*Resistance to fade.*—Good.

*Quantity.*—12 to 15.

*Veins.*—Small, hardly noticeable on upper side.

Reproductive organs:

*Stamens.*—Quantity — Numerous. Color — 1 Light Cream. Size — Small.

*Pollen cups color.*—2 Mimosa.

*Style color.*—1 Light cream.

*Ovary color.*—73 Grass Green.

*Nectar cups color.*—1 Cream.

I claim:

1. A new and distinct variety of poinsettia plant as herein shown and described, particularly characterized by its brilliant cream colored bracts against a background of dark green foliage, its strong, fixed stems, its long lasting keeping qualities in the home, its excellent resistance to fade, vigorous growth habits and its branch and bract production.

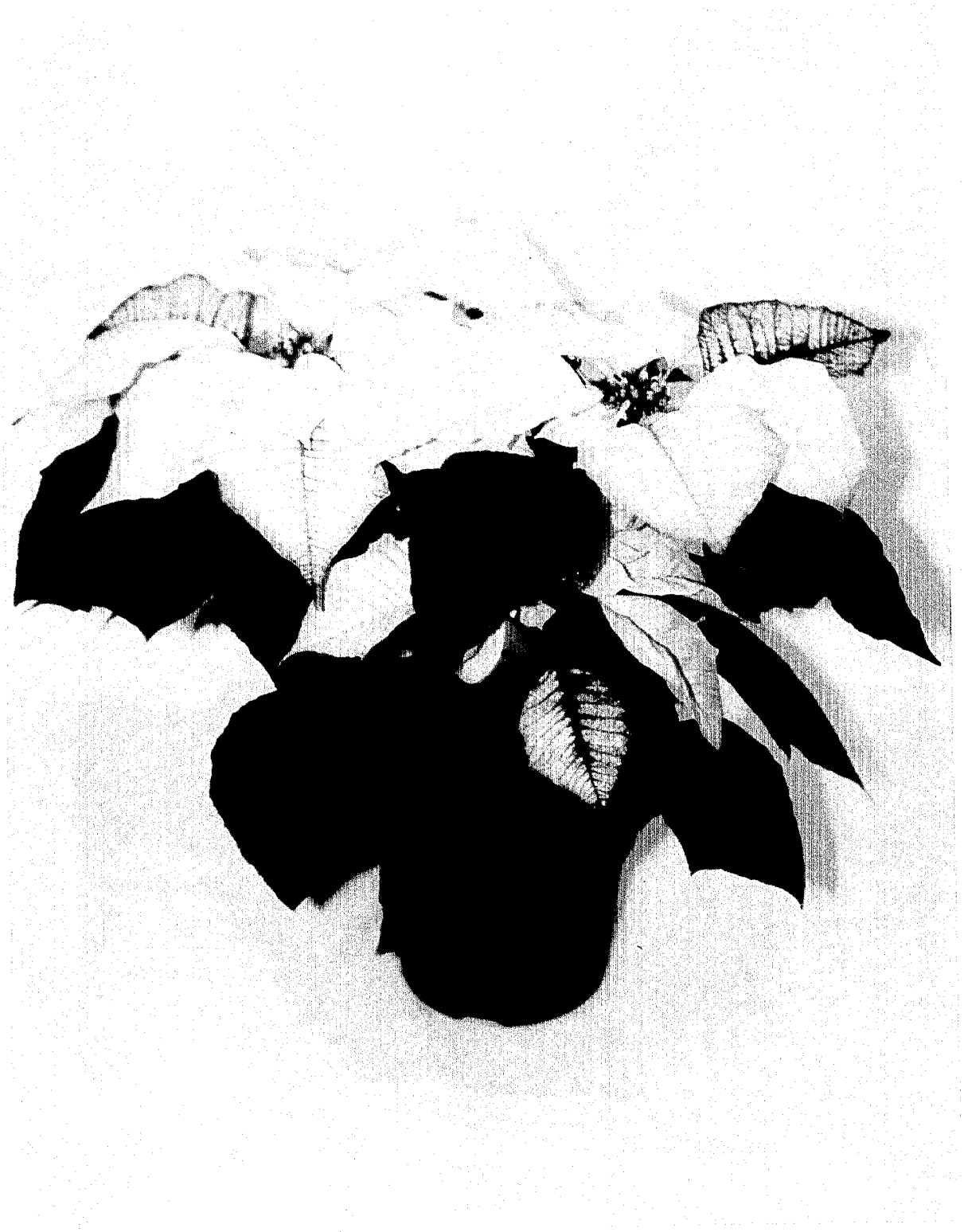

* * * * *